(12) United States Patent
Messerschmid et al.

(10) Patent No.: US 9,907,756 B2
(45) Date of Patent: Mar. 6, 2018

(54) CAPSULE PHARMACEUTICAL DOSAGE FORM COMPRISING A SUSPENSION FORMULATION OF AN INDOLINONE DERIVATIVE

(71) Applicant: Boehringer Ingelheim International GmbH, Ingelheim am Rhein (DE)

(72) Inventors: Roman Messerschmid, Kobe (JP); Rudolf Binder, Mittelbiberach (DE); Thomas Bock, Walchwil (CH); Werner Brox, Beerfelden (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 3 days.

(21) Appl. No.: 15/204,277

(22) Filed: Jul. 7, 2016

(65) Prior Publication Data
US 2016/0324791 A1 Nov. 10, 2016

Related U.S. Application Data

(63) Continuation of application No. 14/877,132, filed on Oct. 7, 2015, now abandoned, which is a continuation of application No. 14/015,186, filed on Aug. 30, 2013, now abandoned, which is a continuation of application No. 12/995,869, filed as application No. PCT/EP2009/056878 on Jun. 4, 2009, now abandoned.

(30) Foreign Application Priority Data

Jun. 6, 2008 (EP) ..................... 08157748

(51) Int. Cl.
*A61K 9/48* (2006.01)
*A61K 31/404* (2006.01)
*A61K 31/496* (2006.01)

(52) U.S. Cl.
CPC .............. *A61K 9/4825* (2013.01); *A61K 9/48* (2013.01); *A61K 9/4816* (2013.01); *A61K 9/4858* (2013.01); *A61K 9/4866* (2013.01); *A61K 31/404* (2013.01); *A61K 31/496* (2013.01)

(58) Field of Classification Search
None
See application file for complete search history.

(56) References Cited

U.S. PATENT DOCUMENTS

| 2,870,062 | A  | 1/1959  | Stanley et al. |
| 4,780,316 | A  | 10/1988 | Brox |
| 5,817,323 | A  | 10/1998 | Hutchinson et al. |
| 7,119,093 | B2 | 10/2006 | Roth et al. |
| 7,176,221 | B2 | 2/2007  | Gierer |
| 2005/0043233 | A1 | 2/2005 | Stefanic et al. |
| 2006/0142373 | A1 | 6/2006 | Park et al. |
| 2006/0293260 | A1 | 12/2006 | Albright |
| 2009/0306101 | A1 | 12/2009 | Solca et al. |
| 2010/0233705 | A1 | 9/2010 | Arao et al. |
| 2011/0178099 | A1 | 7/2011 | Stefanic et al. |
| 2011/0190318 | A1 | 8/2011 | Messerschmid et al. |
| 2012/0142703 | A1 | 6/2012 | Van Ryn et al. |
| 2012/0157472 | A1 | 6/2012 | Larsen et al. |

FOREIGN PATENT DOCUMENTS

| WO | 2004013099 A1 | 2/2004 |
| WO | 2004096224 A2 | 11/2004 |
| WO | 2006018182 A1 | 2/2006 |
| WO | 2006067165 A2 | 6/2006 |
| WO | 2007054551 A1 | 5/2007 |
| WO | 2009147212 A1 | 12/2009 |
| WO | 2009147218 A1 | 12/2009 |
| WO | 2009147220 A1 | 12/2009 |
| WO | 2010081817 A1 | 7/2010 |
| WO | 2010103058 A1 | 9/2010 |
| WO | 2010130757 A1 | 11/2010 |

OTHER PUBLICATIONS

Abstract in English for JP-A-2002-291419, dated Oct. 8, 2002.
Abstract in English for JP-A-2005-074303, dated Mar. 24, 2005.
Abstract in English for JP-A-H07-138151, dated May 30, 1995.
Abstract in English for JP-A-S61-058537, dated Mar. 25, 1986.
Hilberg, F. et al., "Efficacy of BIBF 1120, a potent triple angiokinase inhibitor, in models of human non-small cell lung cancer is augmented by chemotherapy." Journal of Thoracic Oncology, 2007, vol. 2, No. 8, Suppl. 4, p. S380.
International Search Report, Form PCT/ISA/210, for corresponding PCT/EP2009/056878; dated Aug. 14, 2009.
Jianming et al., Application of Dispersing System in Pharmaceutics, Associated Press of Beijing Medical University and Peking Union Medical College Press, 1st edition, Apr. 1995, pp. 252-254.

*Primary Examiner* — Alton N Pryor
(74) *Attorney, Agent, or Firm* — Marc Began; David L. Kershner

(57) ABSTRACT

The present invention relates to a suspension formulation containing the active substance 3-Z-[1-(4-(N-((4-methylpiperazin-1-yl)-methylcarbonyl)-N-methyl-amino)-anilino)-1-phenyl-methylene]-6-methoxycarbonyl-2-indolinone-monoethanesulphonate, to a capsule pharmaceutical dosage form containing said suspension formulation, to a process for preparing said suspension formulation, to a process for preparing said capsule comprising said suspension formulation and to the packaging material for the finished capsule.

8 Claims, 4 Drawing Sheets

Figure 1:
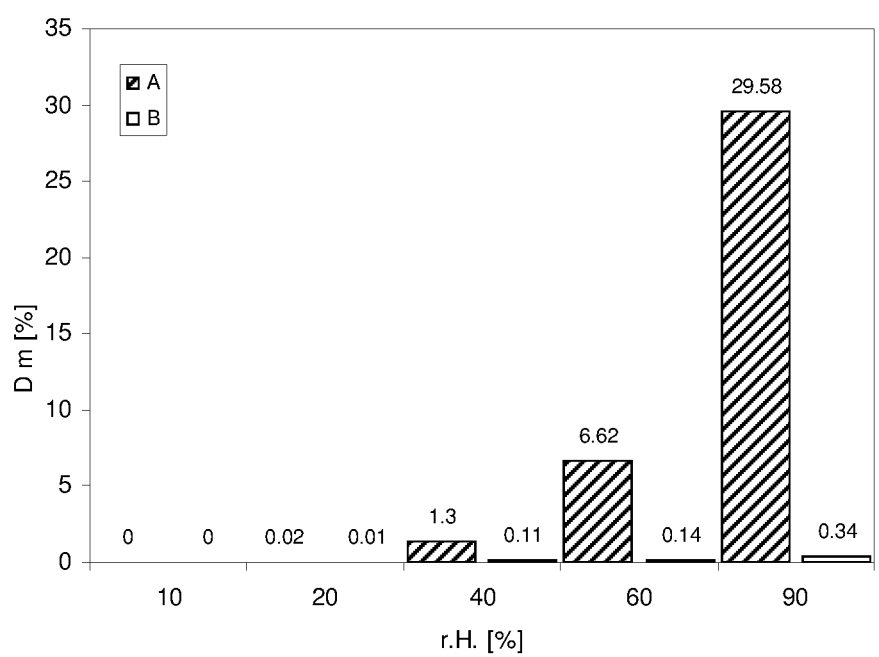

CAPSULE PHARMACEUTICAL DOSAGE FORM COMPRISING A SUSPENSION FORMULATION OF AN INDOLINONE DERIVATIVE

The present invention relates to a suspension formulation containing the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, to a capsule pharmaceutical dosage form containing said suspension formulation, to a process for preparing said suspension formulation, to a process for preparing said capsule comprising said suspension formulation and to the packaging material for the finished capsule.

BACKGROUND TO THE INVENTION

Some pharmacologically active substances may have biopharmaceutical and/or physicochemical properties which make them difficult to formulate into common administration forms. Such substances may be conveniently administered in liquid form either in a lipophilic or hydrophilic carrier system, either as a solution or a suspension, either mixed with a single carrier excipient or mixed with a complex carrier medium made up of several components. Encapsulation of such liquid formulations in soft gelatin capsules potentially offers a very convenient way of administering such pharmacologically active substances.

Solutions

To formulate a solution based system the carrier has to dissolve the active substance. Improved gastrointestinal (GI) absorption of poorly absorbable drugs can be achieved by increasing the dissolution rate of the drug in the presence of bile acids. Within the gastrointestinal tract, bile salts behave as biological detergents that, when mixed with phospholipids, form thermodynamically stable mixed micelles. In many instances the choice of formulation will be limited by solvent capacity, and in others the drug will not be sufficiently soluble in any lipid formulations.

The carrier medium may be designed to spontaneously form an emulsion or microemulsion in the stomach thereby facilitating absorption of the pharmacologically active substance. These systems are commonly known as self (micro-) emulsifying drug delivery systems (SEDDS or SMEDDS). They have to be accurately prepared and even slight variations in the composition cannot be tolerated without irreversibly upsetting the system, and destroying its beneficial properties. For example, the active substance may precipitate out as a consequence of a change in the solubilizing properties of the capsule formulation. This precipitation process may be irreversible and lead to an under-dosing of the patient. The emulsifying properties of the capsule formulation may also be changed, and, upon administration, an emulsion may not be formed in the stomach. As a consequence, the pharmacologically active substance may not be correctly or reproducibly absorbed.

Suspensions

As suspensions do represent thermodynamic instable multiphase systems, various characteristics have to be taken into account during development of these systems. The physical stability of the suspension formulation has to be ensured from the perspective of particle growth as well as from the perspective of re-crystallization in a potential polymorphic form which may have a different solubility or from the perspective of sedimentation associated by caking of the sediment. These factors may influence the liberation of the active substance from the dosage form and hence alter the extent of patient's exposure during the shelf-life of the product. Hence no solubility of the active substance in a single carrier excipient or in the carrier system would be the prerequisite for a physically stable system.

Lipophilic Carrier Systems

Lipophilic excipients are commonly employed as moisture barrier systems to protect chemically instable substances. For this purpose, different types of fats or waxes may be applied on solid dosage forms or on their manufacturing intermediates to prevent migration of ambient water vapour or oxygen and to improve the chemical stability of the active substance. Hot-melt inclusions of the drug into lipophilic binders may as well prevent contact with moisture. Since solid hydrophobic systems poorly disintegrate, drug release in these systems is delayed, in contrast to drug release in low viscous liquid lipid formulations. This delayed drug release is reflected by the specific plasma profiles of the active substance of a modified drug delivery system (Ritschel W. et al., Die Tablette, 2002, 2nd ed., ECV, Aulendorf, p. 2671). Hence, viscosity of liquid systems is a crucial parameter and has to be carefully adjusted to ensure adequate drug release.

In practice lipophilic or 'lipid' formulations are a diverse group of formulations which have a wide range of properties. These result from the blending of up to five classes of excipients, ranging from pure triglyceride oils, through mixed glycerides, lipophilic surfactants, hydrophilic surfactants and water-soluble cosolvents.

Assessment of Quality

The performance of a formulation may be assessed by measuring its relative bioavailability, i.e. comparing its bioavailability with the bioavailability of an aqueous solution of the active substance. If the systems show a comparable bioavailability, not with respect to the dissolution rate but with respect to the drug permeability, pre-systemic or systemic metabolization of the active substance will determine the systemic exposure. Thus, (lipid) suspensions may also show satisfactory exposure of the patient due to the adequate solubility of the active substance within physiological conditions.

3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate is an innovative substance having valuable pharmacological properties, especially for the treatment of oncological diseases, immunologic diseases or pathological conditions involving an immunologic component, or fibrotic diseases.

The chemical structure of this substance is depicted below as Formula (I).

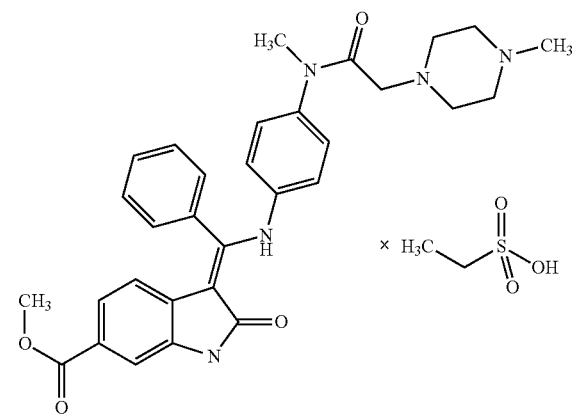

Formula (I)

This substance is described as base in WO 01/27081, as monoethanesulfonate salt form in WO 2004/013099, for its use in the treatment of immunologic diseases or pathological conditions involving an immunologic component in WO 2004/017948, for its use in the treatment of oncological diseases in WO 2004/096224, for its use in the treatment of fibrotic diseases in WO 2006/067165, and as other salt forms in WO 2007/141283.

The aim of the present invention is to obtain for the above drug substance an oral pharmaceutical dosage form which meets adequate chemical stability as well as bioavailability requirements for the desired dosage range tailored to treatment, and a packaging material suitable for the product. Such specific pharmaceutical dosage form is not known from the prior art for this drug substance.

SUMMARY OF THE INVENTION

A first object of the present invention is a formulation of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which comprises a suspension of the active substance.

A further object of the present invention is the above formulation in which the suspension of the active substance is a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate comprising a carrier, a thickener and optionally a glidant/solubilizing agent.

A further object of the present invention is the above formulation in which the carrier is selected from glycerol, acetylated monoglycerides, corn oil glycerides, caprylic-capric triglycerides, medium chain triglycerides, medium chain partial glycerides, caprylic/capric/linoleic triglycerides, caprylic/capric/succinic triglycerides, propylene glycol dicaprylate/dicaprate, ethyl oleate, glycerol mono/dioleate, glycerol monolinolate, macrogolglycerol caprylocaprate, macrogolglycerol linoleate, oleic acid, liquid or semisolid low/intermediate viscous polyethylene glycols (e.g. polyethylene glycol 300, polyethylene glycol 400, polyethylene glycol 600), polyoxyl castor oil, polyoxyl hydrogenated castor oil, propylene glycol monocaprylate, propylene glycol monolaurate, refined animal derived oil, refined soybean oil, refined vegetable oil, sorbitan monostearate, triacetin, triethyl citrate, or mixtures thereof.

In a preferred embodiment in accordance with the present invention, the carrier is a lipid (lipophilic) carrier.

In a preferred embodiment in accordance with the present invention the carrier is selected from the following lipid (lipophilic) carriers: acetylated monoglycerides, corn oil glycerides, medium chain triglycerides, medium chain partial glycerides, caprylic-capric triglycerides, caprylic/capric/linoleic triglycerides, caprylic/capric/succinic triglycerides, propylene glycol dicaprylate/dicaprate, ethyl oleate, glycerol mono/dioleate, glycerol monolinolate, macrogolglycerol caprylocaprate, macrogolglycerol linoleate, oleic acid, polyoxyl castor oil, polyoxyl hydrogenated castor oil, propylene glycol monocaprylate, propylene glycol monolaurate, refined animal derived oil, refined soybean oil, refined vegetable oil, sorbitan monostearate, or mixtures thereof.

A further object of the present invention is the above formulation in which the thickener is selected from semisolid highly viscous or solid polyethyleneglycols (e.g. polyethylene 1000 to 20000), preferably polyethyleneglycols 1000 to 6000, preferably polyethyleneglycol 4000, or oleogel forming excipients, such as Colloidal Silica or Bentonit, or lipophilic or amphiphilic excipients of high viscosity, such as bees wax, glycerol monostearate, hydrogenated vegetable oil, partially hydrogenated vegetable oil or hard fats.

In a preferred embodiment in accordance with the present invention, the thickener is selected from oleogel forming excipients, such as Colloidal Silica or Bentonit, or lipophilic or amphiphilic excipients of high viscosity, such as bees wax, glycerol monostearate, hydrogenated vegetable oil, partially hydrogenated vegetable oil or hard fats.

In a further preferred embodiment, the formulation further comprises a glidant/solubilizing agent.

A further object of the present invention is the above formulation in which the glidant/solubilizing agent is selected from lecithin.

A further object of the present invention is the above formulation comprising a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat and lecithin.

A further object of the present invention is the above formulation which further comprises one or more macrogolglycerols and/or solubilizing agents like lauroyl macrogolglycerides, linoleoyl macrogolglycerides, macrogolglycerol caprylocaprate, macrogolglycerol linolate, oleoyl macrogolglycerides, polyoxyl castor oil, polyoxyl hydrogenated castor oil, polysorbate and propylene glycol monolaurate.

A further object of the present invention is the above formulation, wherein the macrogolglycerols are selected from macrogolglycerol hydroxystearate or macrogolglycerol ricinoleate.

A further object of the present invention is a capsule comprising a capsule shell and a capsule formulation, characterized in that the capsule formulation comprises the above formulation.

A further object of the present invention is the above capsule, characterised in that the capsule is a soft gelatin capsule.

A further object of the present invention is the above capsule, characterised in that the capsule shell comprises glycerol as plasticizing agent.

A further object of the present invention is a capsule comprising a capsule shell and a capsule formulation, characterized in that the capsule formulation comprises the above formulation and in that the capsule is a hard gelatin or a hydroxypropylmethylcellulose (HPMC) capsule, a polyvinyl alcohol polymer capsule or a pullulan capsule, optionally with a sealing or banding.

A further object of the present invention is the above defined formulation or the above defined capsule for use as medicament.

A further object of the present invention is the above defined formulation or the above defined capsule for use as pharmaceutical composition with an antiproliferative activity.

A further object of the present invention is the above defined formulation or the above defined capsule for the treatment of a disease or condition selected from oncological diseases, immunologic diseases or pathological conditions involving an immunologic component, and fibrotic diseases.

A further object of the present invention is the use of the above defined formulation or the above defined capsule for the preparation of a medicament for the treatment of a disease or condition selected from oncological diseases, immunologic diseases or pathological conditions involving an immunologic component, and fibrotic diseases.

A further object of the present invention is a process for the treatment and/or prevention of a disease or condition selected from oncological diseases, immunologic diseases or pathological conditions involving an immunologic component, and fibrotic diseases, characterised in that an effective amount of the above defined formulation or the above defined capsule is administered orally to a patient once or several times daily.

A further object of the present invention is the above defined formulation or the above defined capsule for use in a dosage range of from 0.1 mg to 20 mg of active substance/kg body weight, preferably 0.5 mg to 4 mg active substance/kg body weight.

A further object of the present invention is a glass container or flexible/hard plastic container suitable for the packaging of capsules, containing one or more of the above defined capsules.

A further object of the present invention is an aluminium pouch or double poly bag suitable for the packaging of capsules, containing one or more of the above defined capsules.

A further object of the present invention is a plastic (e.g. PVC, PVDC or Aclar®) blister suitable for the packaging of capsules, containing one or more of the above defined capsules, optionally with an over-packaging of an aluminium pouch.

A further object of the present invention is an aluminium blister suitable for the packaging of capsules, containing one or more of the above defined capsules.

LEGEND TO THE FIGURES

FIG. 1—Mass gain by moisture sorption (Dm in %) under different relative humidity conditions (r.H. in %) for a soft gelatin capsule (A) and for a lipid suspension formulation (B).

Figure 2:
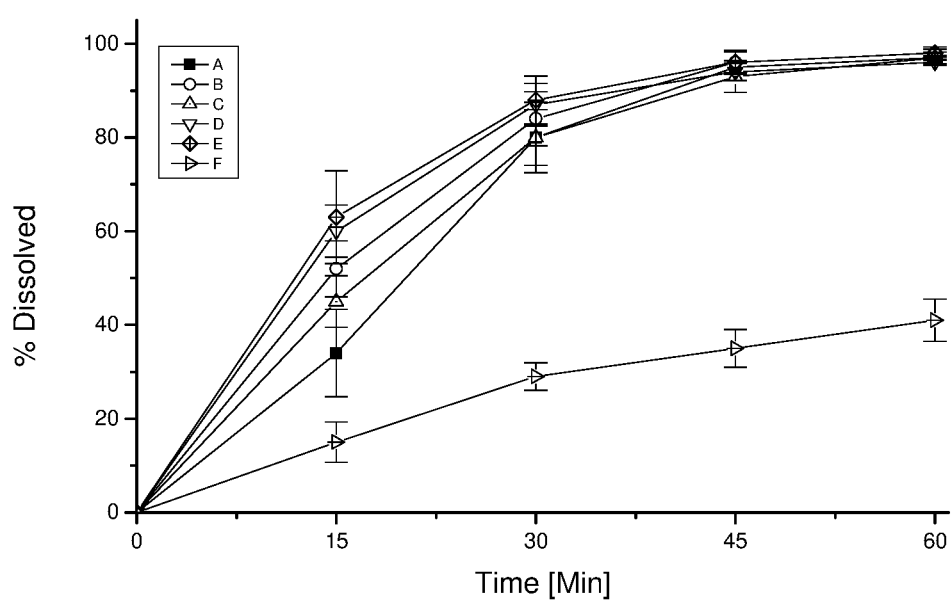

FIG. 2—Effect of the employed lecithin amount on the in-vitro dissolution behaviour (in % of dissolution) over time (in minutes) of soft gelatin capsules: (A) 30% lecithin of preferred amount, (B) 75% lecithin of preferred amount, (C) 90% lecithin of preferred amount, (D) preferred amount of lecithin (equals to 100%), (E) 200% lecithin of preferred amount, (F) 0% lecithin.

Figure 3:
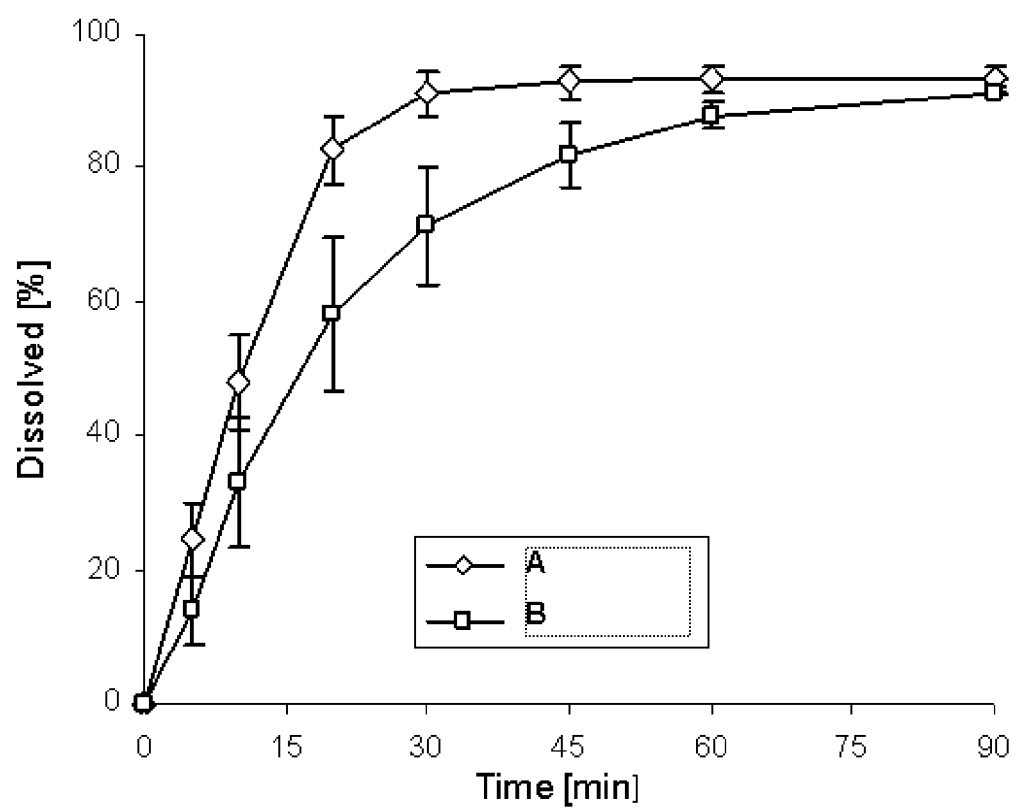

FIG. 3—Effect of the melting range of the hard fat on the in-vitro dissolution behaviour (in % of dissolution) over time (in minutes) of soft gelatin capsules: (A) melting range of 33° C.-40° C., (B) melting range of 40° C.-44° C.

Figure 4:
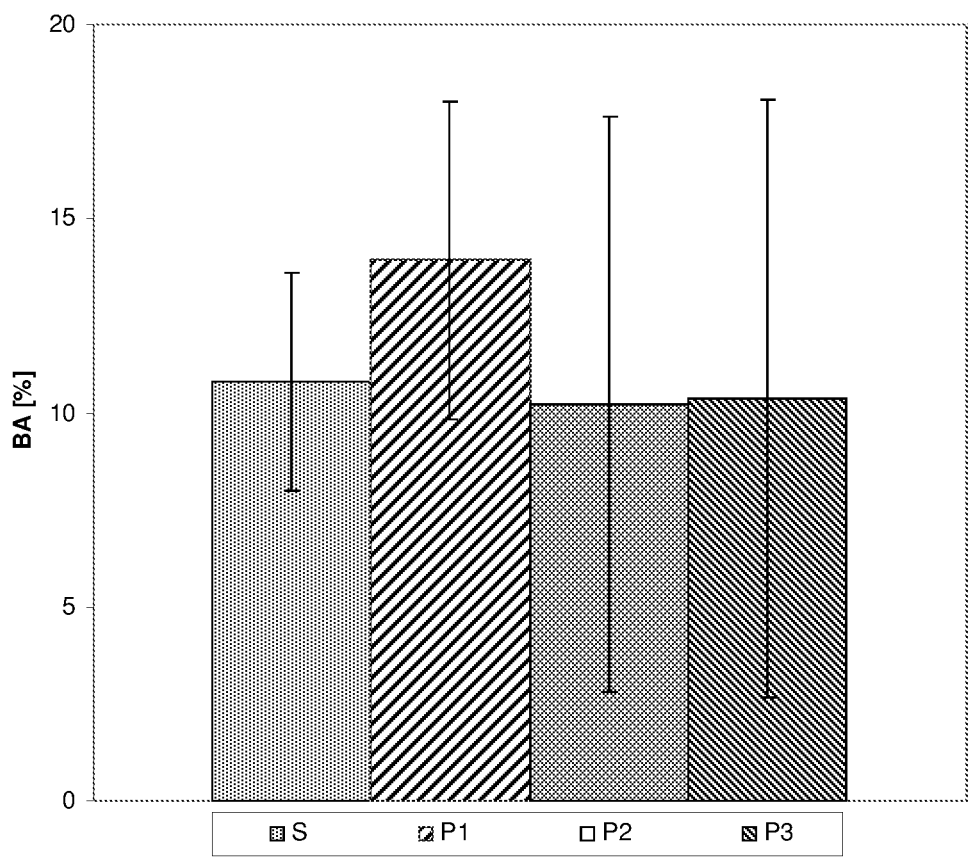

FIG. 4—Comparison of the absolute bioavailability (BA in %) tested in the rat over 24 hours for the aqueous solution (S) versus different carrier systems (P1, P2 and P3) of the active substance—Error bars indicate standard deviations.

DETAILED DESCRIPTION OF THE INVENTION

It has been found that, surprisingly, a soft gelatin capsule including a liquid formulation comprising a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat and lecithin, meets the adequate bioavailability requirements for the desired dosage range tailored to treatment with the drug substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate. This liquid formulation consists of a lipid suspension of the active substance.

An advantage of such soft gelatin capsule containing a lipid suspension is that the water uptake into the formulation is very unlikely. The dosage form is divided into three different compartments, namely (a) a hydrophilic capsule shell and (b) the hydrophobic carrier system in which (c) the slightly hygroscopic powder of active substance is suspended. Due to ambient moisture the content of water may vary within these different compartments. It will migrate by diffusion until an equilibrium state is reached. The water content may affect different properties of the drug product, such as the chemical stability of the active substance (predominantly via hydrolysis) or the elasticity of the capsule shell. The water uptake in the present system is primarily in the capsule shell. This can be shown by water vapour sorption experiments (shown in FIG. 1) as well as by the correlation of the mass gain with the softening of the capsule. The water uptake does further not affect the chemical stability of the drug substance. This is confirmed by the stress stability studies of, for example, 1 month at 70° C., and by the long-term (3 years) and accelerated (6 months) stability study results for the systems in accordance with the present invention.

Furthermore, studies have shown that there is no mass increase or sticking problem for the capsules in accordance with the present invention when stored in tight packaging materials. Thus, recommended packaging for such capsules are, for example, alu/alu blisters and HDPE bottles.

Generally, soft gelatin capsules have a capsule shell made of gelatin, one or more plasticizing agents, in particular glycerol, optionally further auxiliary materials, such as dyes, colorant pigments, flavouring agents, sugar, oligosaccharides or polysaccharides, and a capsule formulation (or capsule filling) containing a solvent, adjuvants and one or more pharmacologically active substances. The term gelatin as used herein includes not only unmodified gelatin as in the European Pharmacopeia but also modified gelatin, such as for example succinated gelatin.

As already mentioned hereinbefore, the present invention relates to a lipid suspension formulation of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

In a preferred embodiment in accordance with the present invention, the lipid suspension formulation of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate comprises a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in a lipid carrier, a thickener and a glidant/solubilizing agent.

In a further preferred embodiment in accordance with the present invention, the amount of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate is comprised within the range of 1 to 90 weight % of the lipid suspension formulation, preferably within 10 and 50%.

To avoid the above-mentioned physical stability issues, such as re-crystallization or particle-growth, the active substance must be either completely insoluble or dissolved in the carrier. A solubility screening of lipophilic hydrophilic and amphiphilic excipients and mixtures revealed various potential carriers for formulating the lipid suspension in accordance with the present invention. The choice of these lipid carriers for the lipid suspension in accordance with the present invention represents a further object of the present invention.

Thus, in a preferred embodiment, suitable carriers or carrier components for the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate are acetylated monoglycerides, corn oil glycerides, ethyl oleate, glycerol mono/dioleate, glycerol monolinolate, macrogolglycerol caprylocaprate, macrogolglycerol linoleate, medium chain partial glycerides, medium chain triglycerides, caprylic-capric triglycerides, caprylic/capric/linoleic triglycerides, caprylic/capric/succinic triglycerides, propylene glycol dicaprylate/dicaprate, oleic acid polyoxyl castor oil, polyoxyl hydrogenated castor oil, propylene glycol monocaprylate, propylene glycol monolaurate, refined animal derived oil, refined soybean oil, refined vegetable oil, sorbitan monostearate, triacetin, triethyl citrate, or mixtures thereof.

Stability issues such as hydrolytic degradation of the active substance may also be caused by hydrophilic carrier components. Therefore, carrier systems based on hydrophilic polyethylene glycols will generally show inferior stability than more hydrophobic carriers such as lipid carriers.

In accordance with the present invention, the most preferred lipid carrier is medium chain triglycerides. It is comprised within the range of 1 to 90 weight % of the lipid suspension formulation, preferably within 10 and 70%. Suitable medium chain triglycerides may be the commercial product Miglyol 812®, Miglyol 810®, Miglyol 818®, Miglyol 829® or Miglyol 840®.

A thickener adjusts the viscosity of the suspension. It stabilizes the suspension system, ensures optimal processing and guarantees an adequate capsule quality, especially as far as content uniformity or dissolution behaviour are concerned. In a preferred embodiment, suitable thickeners to be used in the present invention are oleogel forming excipients, such as Colloidal Silica or Bentonit, or lipophilic or amphiphilic excipients of high viscosity, such as bees wax, glycerol monostearate, hydrogenated vegetable oil, partially hydrogenated vegetable oil or hard fats.

In accordance with the present invention, the most preferred thickener is hard fat. It is preferably comprised within the range of 1 to 30 weight % of the suspension formulation, most preferably within 10 and 30 weight %. The most suitable hard fats have a melting range of 30° C. to 44° C., most preferably a melting range of 33° C. to 40° C. Suitable commercially available products are Gelucire® 33/01, Witepsol® W35 or Softisan® 378. The determination of the most suitable melting range for hard fats can be performed as shown in FIG. 3, by measurement of the effect of the melting range of the hard fat on the in-vitro dissolution behaviour over time.

Lecithin is a common excipient for carrier-systems in soft gelatin capsules. It is used as a glidant of the highly concentrated suspension during encapsulation, prevents blocking of ducts and pumps and ensures high mass uniformity of the encapsulated formulation. Furthermore Lecithin acts as a surfactant, which may improve distribution of the formulation-droplets during in-vitro dissolution testing as well as in-vivo for drug resorption. Furthermore it may also improve wetting of the active substance crystals. Suitable lecithin may be the commercial product Topcithin®.

It was surprisingly found that lecithin, up to a certain content, is useful to improve the dissolution behaviour of the finished capsules. Exceeding amounts do not show an additional benefit during in-vitro dissolution testing, as shown in FIG. 2.

In a preferred embodiment in accordance with the present invention, the amount of lecithin is comprised within the range of 0.1 to 10 weight % of the lipid suspension formulation, most preferably within 0.25 and 2.5%.

In an alternative embodiment, the present invention relates to a lipid suspension formulation of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, comprising a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat, lecithin and one or more macrogolglycerols, such as for example macrogolglycerol-hydroxystearate (traded for example under the name Eumulgin® HRE 40 PH) or macrogolglycerol-ricinoleate (also known as polyoxyl castor oil and traded for example under the name Cremophor® EL, Cremophor® RH40 or Eumulgin® RO 35 PH).

In a preferred embodiment in accordance with the present invention, the amount of macrogolglycerol(s) is comprised within the range of 0.1 to 50 weight % of the lipid suspension formulation, most preferably within 0.3 and 10%.

Three carrier systems (the hydrophilic P3, lipophilic P1 and lipophilic with surfactants P2 semi-solid suspension formulations described in the foregoing) were tested for bioavailability in non-clinical studies and all of them were identified to be suitable options for an oral dosage form of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

However, for reasons of bioavailability, as is evident from the results shown in FIG. 4, lipid (lipophilic) suspension formulations comprising a viscous suspension of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate in medium chain triglycerides, hard fat and lecithin are preferred.

Hence, FIG. 4 shows the results of a comparison of the absolute bioavailability (BA in %) tested in the rat over 24 hours for the aqueous solution (S) versus different carrier systems (P1, P2 and P3) of the active substance in accordance with the present invention. The experiment is described in the following.

The table below shows the composition of the tested carrier systems (semi-solid suspension formulations).

| Ingredients | Formulation | | |
| --- | --- | --- | --- |
| | P1 | P2 [%]* | P3 |
| Active Substance | 43.48 | 42.19 | 31.75 |
| Triglycerides, Medium-Chain | 37.83 | 41.77 | — |
| Hard fat | 18.26 | 12.66 | — |
| Cremophor RH40 | — | 2.95 | — |
| Lecithin | 0.43 | 0.42 | — |
| Glycerol 85% | — | — | 3.17 |
| Purified Water | — | — | 4.76 |
| Macrogol 600 | — | — | 58.10 |
| Macrogol 4000 | — | — | 2.22 |

*slight deviations of the quantities towards 100 percent may be caused by rounding errors The semi-solid suspensions are filled in hard gelatin capsules (Capsugel, no. Y0303490). Each capsule contains approximately 15 to 20 mg of the formulation. The capsules are applied to the rats with a special device similar to gavage. For comparison an aqueous solution containing 0.5% Natrosol 250 HX is applied via gavage. For calculation of the absolute bioavailability an additional group of rats is dosed intravenously with the compound dissolved in 5% glucose solution (aqueous solution (S)). 5 male Han Wistar rats (strain: CrlGlxBrlHan:WI) are used per group. Blood sampling times are 0.5 h, 1 h, 2 h, 4 h, 8 h, 24 h post dose and plasma is analysed by a validated HPLC/MS/MS method. From the plasma level time curves areas under the curve (AUC) are calculated by linear trapezoidal rule. Dose normalised AUCs of the oral formulation are divided by dose normalised AUCs of the intravenous formulation for the calculation of the absolute bioavailability. As can be seen from the results of the experiment shown in FIG. 4, the bioavailability is similar for the aqueous solution (S: 11%) and the different carrier systems of active substance (P1: 14%, P2: 10% and P3: 10%), however the inter-individual variation (standard deviation of bioavailability) is smaller for the aqueous solution (S) and the carrier system (P1) when compared to the carrier systems (P2) and (P3) (2.8 and 4.1 versus 7.4 and 7.1), indicating a practically complete relative bioavailability for the tested formulations (P1, P2 and P3) versus the solution (S) but a higher variation in the carrier systems (P2) and (P3).

The present invention further relates to a capsule pharmaceutical dosage form consisting of a capsule shell and a capsule formulation (or capsule filling), characterized in that the capsule formulation (or capsule filling) comprises the lipid suspension formulation as hereinbefore described. The capsule pharmaceutical dosage form may be a soft gelatine capsule, a hard gelatine capsule, or an hydroxypropylmethylcellulose (HPMC) capsule or a polyvinyl alcohol polymer capsule or a pullulan capsule.

In the case of a hard gelatine capsule or an hydroxypropylmethylcellulose (HPMC) capsule, a polyvinyl alcohol polymer capsule or a pullulan capsule, the filled in capsule may further be sealed or banded.

In a preferred embodiment in accordance with the present invention, the capsule is a soft gelatin capsule consisting of a capsule shell comprising gelatin, one or more plasticizing agents and optionally further auxiliary materials, and a capsule formulation (or capsule filling), characterized in that the capsule formulation (or capsule filling) comprises the lipid suspension formulation as hereinbefore described.

The capsule pharmaceutical dosage form according to the invention, and especially the soft gelatin capsules, may be stored in suitable glass containers or in flexible/hard plastic containers, preferably non-PVC materials based, or in plastic (e.g. PVC, PVDC or Aclar®) blisters optionally with an over-packaging of aluminium (aluminium pouch), or in aluminium blisters consisting of e.g a bottom foil of PA/Al/PVC and an aluminium lidding foil, the later providing the highest water protection. Hence, the containers may be designed so as to provide particular protection for the capsule pharmaceutical dosage form according to the invention, and especially the soft gelatin capsules, e.g. to protect them from light, oxygen or water. Flexible plastic containers may contain additional protection, e.g. in the form of an additional aluminium packaging.

The capsule pharmaceutical dosage form according to the invention may be prepared by conventional methods of producing capsules known from the literature. The soft gelatin capsule according to the invention may be prepared by conventional methods of producing soft gelatin capsules known from the literature, such as for example the "rotary die procedure", described for example in Swarbrick, Boylann, Encyclopedia of pharmaceutical technology, Marcel Dekker, 1990, Vol. 2, pp 269 ff or in Lachmann et al., "The Theory and Practice of Industrial Pharmacy", 2nd Edition, pages 404-419, 1976, or other procedures, such as those described for example in Emerson R. F. et al., "Soft gelatin capsule update", Drug Dev. Ind. Pharm., Vol. 12, No. 8-9, pp. 1133-44, 1986.

The lipid suspension formulation may be prepared by conventional methods of producing formulations known from the literature, i.e. by mixing the ingredients at a pre-determined temperature in a pre-determined order in order to obtain a homogenized suspension.

Alternatively, the lipid suspension formulation may be prepared in accordance with the procedure described in Example 10, which is also an object of the present invention Lipid suspension formulation of the active substance, finished soft gelatin capsules containing same and packaging materials for the packaging of finished soft gelatin capsules according to the invention are illustrated by the Examples and Figures that follow. The Examples serve purely as an illustration and are not to be construed in a limiting capacity.

Examples of Carrier Systems (Formulations), Soft Gelatin Capsules, Packaging Materials, and of a Manufacturing Process for the Preparation of a Lipid Suspension Formulation of the Active Substance The active substance in all the Examples is 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

EXAMPLE 1

Lipid Based Carrier System

| | Formulation | | |
|---|---|---|---|
| Ingredients | A | B [%]* | C |
| Active Substance | 43.48 | 43.48 | 43.48 |
| Triglycerides, Medium-Chain | 28.70 | 37.83 | 38.045 |
| Hard fat | 27.39 | 18.26 | 18.26 |
| Lecithin | 0.43 | 0.43 | 0.215 |

*slight deviations of the quantities towards 100 percent may be caused by rounding errors

EXAMPLE 2

Lipid Based Carrier System with Additional Surfactant

| Ingredients | [%]* |
|---|---|
| Active Substance | 42.19 |
| Triglycerides, Medium-Chain | 41.77 |
| Hard fat | 12.66 |
| Cremophor RH40 | 2.95 |
| Lecithin | 0.42 |

*slight deviations of the quantities towards 100 percent may be caused by rounding errors

EXAMPLE 3

Hydrophilic Carrier System

| Ingredients | [%]* |
|---|---|
| Active Substance | 31.75 |
| Glycerol 85% | 3.17 |

| Ingredients | [%]* |
|---|---|
| Purified Water | 4.76 |
| Macrogol 600 | 58.10 |
| Macrogol 4000 | 2.22 |

*slight deviations of the quantities towards 100 percent may be caused by rounding errors

EXAMPLE 4

Soft Gelatin Capsule Containing 50 mg of Active Substance

| Ingredients | Function | Formulation A mg per capsule | Formulation B mg per capsule | Formulation C mg per capsule |
|---|---|---|---|---|
| Active Substance* | Active Ingredient | 60.20 | 60.20 | 60.20 |
| Triglycerides, Medium-chain | Carrier | 40.95 | 53.70 | 54.00 |
| Hard fat | Thickener | 38.25 | 25.50 | 25.50 |
| Lecithin | Wetting agent/Glidant | 0.60 | 0.60 | 0.30 |
| Gelatin | Film-former | 72.25 | 72.25 | 72.25 |
| Glycerol 85% | Plasticizer | 32.24 | 32.24 | 32.24 |
| Titanium dioxide | Colorant | 0.20 | 0.20 | 0.20 |
| Iron oxide A | Colorant | 0.32 | 0.32 | 0.32 |
| Iron oxide B | Colorant | 0.32 | 0.32 | 0.32 |
| Total Capsule Weight | | 245.33 | 245.33 | 245.33 |

*The figures refer to the amount of ethanesulfonate salt (dry basis) equivalent to the labeled amount of the free base

EXAMPLE 5

Soft Gelatin Capsule Containing 100 mg of Active Substance

| Ingredients | Function | Formulation A mg per capsule | Formulation B mg per capsule | Formulation C mg per capsule |
|---|---|---|---|---|
| Active Substance* | Active Ingredient | 120.40 | 120.40 | 120.40 |
| Triglycerides, Medium-chain | Carrier | 81.90 | 107.40 | 106.8 |
| Hard fat | Thickener | 76.50 | 51.00 | 51.00 |
| Lecithin | Wetting agent/Glidant | 1.20 | 1.20 | 1.80 |
| Gelatin | Film-former | 111.58 | 111.58 | 111.58 |
| Glycerol 85% | Plasticizer | 48.79 | 48.79 | 48.79 |
| Titanium dioxide | Colorant | 0.36 | 0.36 | 0.36 |
| Iron oxide A | Colorant | 0.06 | 0.06 | 0.06 |
| Iron oxide B | Colorant | 0.17 | 0.17 | 0.17 |
| Total Capsule Weight | | 440.96 | 440.96 | 440.96 |

*The figures refer to the amount of ethanesulfonate salt (dry basis) equivalent to the labeled amount of the free base

EXAMPLE 6

Soft Gelatin Capsule Containing 125 mg of Active Substance

| Ingredients | Function | Formulation A mg per capsule | Formulation B mg per capsule | Formulation C mg per capsule |
|---|---|---|---|---|
| Active Substance* | Active Ingredient | 150.50 | 150.50 | 150.50 |
| Triglycerides, Medium-chain | Carrier | 102.375 | 134.25 | 133.5 |
| Hard fat | Thickener | 95.625 | 63.75 | 63.75 |
| Lecithin | Wetting agent/Glidant | 1.50 | 1.50 | 2.25 |
| Gelatin | Film-former | 142.82 | 142.82 | 142.82 |
| Glycerol 85% | Plasticizer | 62.45 | 62.45 | 62.45 |
| Titanium dioxide | Colorant | 0.47 | 0.47 | 0.47 |
| Iron oxide A | Colorant | 0.08 | 0.08 | 0.08 |
| Iron oxide B | Colorant | 0.22 | 0.22 | 0.22 |
| Total Capsule Weight | | 556.04 | 556.04 | 556.04 |

*The figures refer to the amount of ethanesulfonate salt (dry basis) equivalent to the labeled amount of the free base

EXAMPLE 7

Soft Gelatin Capsule Containing 150 mg of Active Substance

| Ingredients | Function | Formulation A mg per capsule | Formulation B mg per capsule | Formulation C mg per capsule |
|---|---|---|---|---|
| Active Substance* | Active Ingredient | 180.60 | 180.60 | 180.60 |
| Triglycerides, Medium-chain | Carrier | 122.85 | 161.10 | 160.20 |
| Hard fat | Thickener | 114.75 | 76.50 | 76.50 |
| Lecithin | Wetting agent/Glidant | 1.80 | 1.80 | 2.70 |
| Gelatin | Film-former | 142.82 | 142.82 | 142.82 |
| Glycerol 85% | Plasticizer | 62.45 | 62.45 | 62.45 |
| Titanium dioxide | Colorant | 0.47 | 0.47 | 0.47 |
| Iron oxide A | Colorant | 0.08 | 0.08 | 0.08 |
| Iron oxide B | Colorant | 0.22 | 0.22 | 0.22 |
| Total Capsule Weight | | 626.04 | 626.04 | 626.04 |

*The figures refer to the amount of ethanesulfonate salt (dry basis) equivalent to the labeled amount of the free base

EXAMPLE 8

Soft Gelatin Capsule Containing 200 mg of Active Substance

| Ingredients | Function | Formulation A mg per capsule | Formulation B mg per capsule | Formulation C mg per capsule |
|---|---|---|---|---|
| Active Substance* | Active Ingredient | 240.80 | 240.80 | 240.80 |

-continued

| Ingredients | Function | Formulation A mg per capsule | Formulation B mg per capsule | Formulation C mg per capsule |
|---|---|---|---|---|
| Triglycerides, Medium-chain | Carrier | 163.30 | 214.80 | 216.00 |
| Hard fat | Thickener | 153.50 | 102.00 | 102.00 |
| Lecithin | Wetting agent/ Glidant | 2.40 | 2.40 | 1.20 |
| Gelatin | Film-former | 203.19 | 203.19 | 203.19 |
| Glycerol 85% | Plasticizer | 102.61 | 102.61 | 102.61 |
| Titanium dioxide | Colorant | 0.57 | 0.57 | 0.57 |
| Iron oxide A | Colorant | 0.90 | 0.90 | 0.90 |
| Iron oxide B | Colorant | 0.90 | 0.90 | 0.90 |
| Total Capsule Weight | | 868.17 | 868.17 | 868.17 |

*The figures refer to the amount of ethanesulfonate salt (dry basis) equivalent to the labeled amount of the free base

EXAMPLE 9

Packaging materials for the packaging of the soft gelatin capsules of above examples 4 to 8 may be glass containers, flexible/hard plastic containers or PVC/PVDC blisters, optionally within an aluminium pouch, or alu/alu blisters.

EXAMPLE 10

In the following, a manufacturing process for the preparation of a lipid suspension formulation of the active substance and a process for the encapsulation are described.

a: Hard fat and parts of Medium-chain triglycerides are pre-mixed in the processing unit. Subsequently lecithin, the rest of medium-chain triglycerides and the active substance are added. The suspension is mixed, homogenized, deaerated and finally sieved to produce the formulation (Fillmix).

b. The gelatin basic mass components (glycerol, water and gelatine) are mixed and dissolved at elevated temperature. Then, the corresponding colours are added and mixed, producing the Coloured Gelatin Mass.

c. After adjustment of the encapsulation machine, Fillmix and Coloured Gelatin Mass are processed into soft gelatin capsules using the rotary-die process. This process is e.g. described in Swarbrick, Boylann, Encyclopedia of pharmaceutical technology, Marcel Dekker, 1990, Vol. 2, pp 269 ff.

d. The initial drying is carried out using a rotary dryer. For the final drying step, capsules are placed on trays. Drying is performed at 15-26° C. and low relative humidity.

e. After 100% visual inspection of the capsules for separation of deformed or leaking capsules, the capsules are size sorted.

f. Finally, the capsules are imprinted, using an Offset printing technology or an Ink-jet printing technology. Alternatively, the capsule imprint can be made using the Ribbon printing technology, a technology in which the gelatin bands are imprinted prior to the encapsulation step c.

The invention claimed is:

1. A formulation of the active substance 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate which comprises a lipid suspension of the active substance in 1 to 90 wt. % of medium chain triglycerides, 1 to 30 wt. % of hard fat and 0.1 to 10 wt. % of lecithin.

2. A capsule comprising a capsule shell and a capsule formulation, wherein the capsule formulation comprises the formulation in accordance with claim 1.

3. The capsule according to claim 2, wherein the capsule is a soft gelatin capsule.

4. The capsule according to claim 2, wherein the capsule shell comprises glycerol as plasticizing agent.

5. The capsule according to claim 2, wherein the capsule is a hard gelatin or a hydroxypropylmethylcellulose (HPMC) capsule, a polyvinyl alcohol polymer capsule or a pullulan capsule, optionally with a sealing or banding.

6. A lipid suspension consisting essentially of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, medium chain triglycerides, hard fat and lecithin, wherein the medium chain triglycerides, hard fat and lecithin are present in the lipid suspension in the following amounts:

1 to 90 wt. % of medium chain triglycerides,
1 to 30 wt. % of hard fat, and
0.1 to 10 wt. % of lecithin.

7. A capsule comprising a capsule shell and a capsule formulation, wherein the capsule formulation comprises the lipid suspension in accordance with claim 6.

8. The capsule according to claim 7, wherein the capsule is a soft gelatin capsule.

* * * * *